(12) United States Patent
Raistrick et al.

(10) Patent No.: US 6,877,658 B2
(45) Date of Patent: Apr. 12, 2005

(54) APPARATUS AND METHOD FOR INFORMATION CHALLENGED PERSONS TO DETERMINE INFORMATION REGARDING PHARMACEUTICAL CONTAINER LABELS

(75) Inventors: David Raistrick, Peoria, IL (US); Philip Raistrick, Normal, IL (US)

(73) Assignee: En-Vision America, Inc., Normal, IL (US)

( * ) Notice: Subject to any disclaimer, the term of this patent is extended or adjusted under 35 U.S.C. 154(b) by 199 days.

(21) Appl. No.: 09/761,935

(22) Filed: Jan. 17, 2001

(65) Prior Publication Data

US 2003/0189089 A1 Oct. 9, 2003

Related U.S. Application Data

(63) Continuation-in-part of application No. 09/490,681, filed on Jan. 24, 2000.

(51) Int. Cl.$^7$ .............................. G06F 17/60; G06K 7/10
(52) U.S. Cl. .................................. 235/385; 235/462.01
(58) Field of Search ................................ 235/385, 375, 235/380, 462, 472.01, 381, 383, 462.01, 462.48

(56) References Cited

U.S. PATENT DOCUMENTS

| | | |
|---|---|---|
| 4,857,716 A | 8/1989 | Gombrich et al. |
| 5,177,800 A | 1/1993 | Coats |
| 5,289,157 A | 2/1994 | Rudick et al. |
| 5,291,399 A | 3/1994 | Chaco |
| 5,319,185 A | 6/1994 | Obata |
| 5,340,972 A | 8/1994 | Sandor |
| 5,347,453 A | 9/1994 | Maestre |
| 5,408,443 A | 4/1995 | Weinberger |
| 5,410,140 A | 4/1995 | Bard et al. |
| 5,465,082 A | 11/1995 | Chaco |
| 5,495,961 A | 3/1996 | Maestre |
| 5,557,096 A | 9/1996 | Watanabe et al. |
| 5,577,335 A | 11/1996 | Tucker |
| 5,602,377 A | 2/1997 | Beller et al. |
| 5,602,802 A | 2/1997 | Leigh-Spencer et al. |
| 5,616,901 A | 4/1997 | Crandall |
| 5,646,912 A | 7/1997 | Cousin |
| 5,657,236 A | 8/1997 | Conkright |

(Continued)

OTHER PUBLICATIONS

Article from http://wearables.bly.org entitled "Re: Bar Code Search Engine" by David Covin, dated Dec. 12, 1999 (one page).

Press Release from www.connectthings.com entitled "Fast Path to Patient–Fass on the Web" dated Dec. 9, 1999 (one page).

Article from Braille Forum published by the American Council of the entitled "Mastering the Code to Independence" by Nolan Crabb dated Jun. 1998 (three pages).

Article from U.S. News & World Report entitled "Doctoring a Sickly System" by Joseph P. Shapiro, dated Dec. 13, 1999 (two pages).

*Primary Examiner*—Thien M. Le
(74) *Attorney, Agent, or Firm*—Trexler, Bushnell, Giangiorgi, Blackstone & Marr, Ltd.

(57) ABSTRACT

An apparatus and method permitting an information challenged person to determine the content of pharmaceutical information contained in a label placed on a medicine container. The apparatus comprises, in one embodiment, a two-dimensional bar code label and, in a second embodiment, a radio frequency identification label, a reader and a processing unit. The reader scans the label located on the medicine container, the label information is then decoded by a processing unit into text information for audio and/or video dissemination to the information challenged person.

47 Claims, 9 Drawing Sheets

U.S. PATENT DOCUMENTS

| | | | |
|---|---|---|---|
| 5,700,998 A | * 12/1997 | Palti | 235/375 |
| 5,706,258 A | 1/1998 | Poe et al. | |
| 5,708,627 A | 1/1998 | Gormley | |
| 5,719,780 A | 2/1998 | Holmes et al. | |
| 5,745,366 A | 4/1998 | Higham et al. | |
| 5,751,660 A | 5/1998 | Chappell | |
| 5,805,051 A | 9/1998 | Herrmann et al. | |
| 5,812,064 A | 9/1998 | Barbour | |
| 5,812,410 A | 9/1998 | Lion et al. | |
| 5,822,544 A | 10/1998 | Chaco et al. | |
| 5,826,217 A | 10/1998 | Lerner | |
| 5,838,224 A | 11/1998 | Andrews | |
| 5,839,108 A | 11/1998 | Daberko et al. | |
| 5,850,344 A | 12/1998 | Conkright | |
| 5,852,590 A | 12/1998 | de la Huerga | |
| 5,899,335 A | 5/1999 | Boyer et al. | |
| 5,905,653 A | 5/1999 | Higham et al. | |
| 5,912,818 A | 6/1999 | McGrady et al. | |
| 5,915,558 A | 6/1999 | Girvetz | |
| 5,917,174 A | 6/1999 | Moore et al. | |
| 5,963,136 A | 10/1999 | O'Brien | |
| 5,971,279 A | 10/1999 | Raistrick et al. | |
| 5,971,594 A | 10/1999 | Sahai et al. | |
| 5,990,782 A | 11/1999 | Lee | |
| 5,992,742 A | * 11/1999 | Sullivan et al. | 235/462.01 |
| 6,004,020 A | 12/1999 | Bartur | |
| 6,014,346 A | 1/2000 | Malone | |
| 6,088,695 A | 7/2000 | Kara | |
| 6,150,942 A | 11/2000 | O'Brien | |
| 6,588,670 B1 | * 7/2003 | Bukowski | 235/462.45 |
| 6,637,649 B1 | * 10/2003 | Walsh | 235/380 |

* cited by examiner

FIGURE 3
FIGURE 4
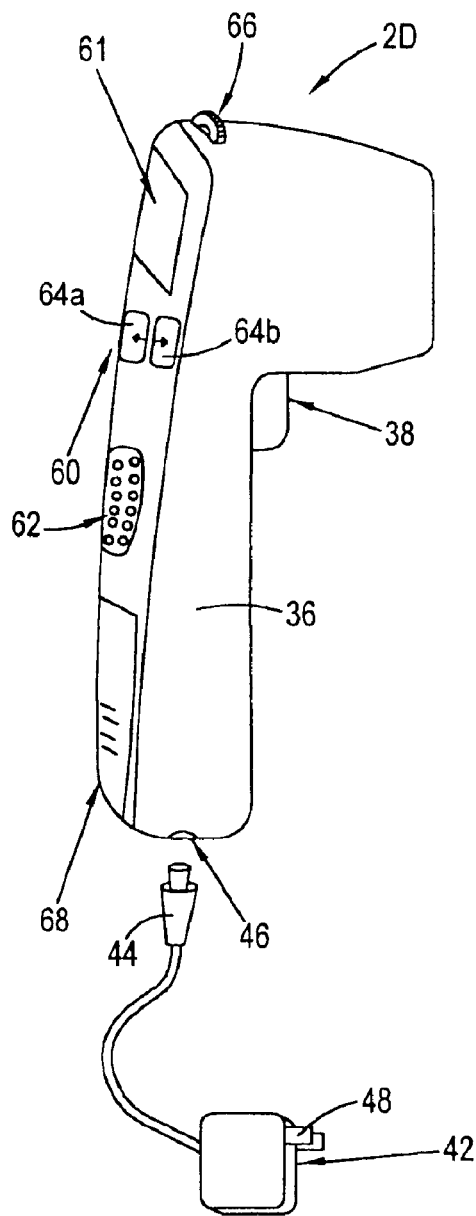
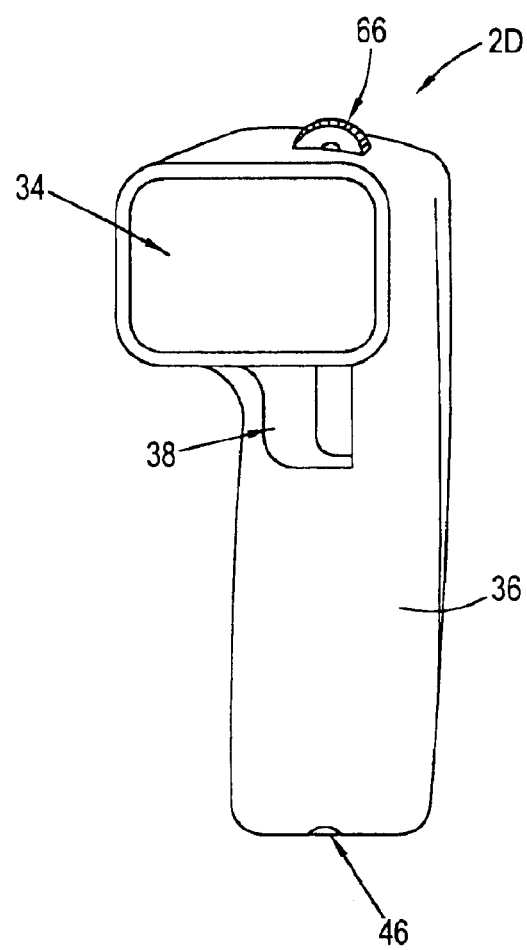

APPARATUS AND METHOD FOR INFORMATION CHALLENGED PERSONS TO DETERMINE INFORMATION REGARDING PHARMACEUTICAL CONTAINER LABELS

This application is a continuation-in-part application of U.S. patent application Ser. No. 09/490,681, filed on Jan. 24, 2000 and entitled "Apparatus and Method for Visually Impaired Users to Read Pharmaceutical Container Labels".

BACKGROUND OF THE INVENTION

The present invention relates to scanning devices and, more particularly, to an apparatus and method that enables a visually impaired person or other information challenged person to use a scanning device to determine information provided on a label, such as a two-dimensional bar code label or a radio identification (RFID) label, which is placed on a medicine container.

Typically, with each medicine prescribed and filled, there is placed on the medicine container a text label that contains written information specific to that medication. A significant problem for the visually impaired or other information challenged persons is that they cannot read the text information provided on their medicine container and, therefore, must rely upon a third party to read the information to them. Thus, the visually impaired or other information challenged person who strive to lead independent lives are forced to remain dependent upon others for the simplest of tasks and, depending upon the medication, reveal information of a very personal nature. In addition, because of the limited amount of space on the label, information which would be helpful cannot be provided because of space limitations.

Attempts have been made in the past to permit visually impaired individuals more independence through the use of scanning devices. However, the prior art does not contemplate nor is it practical for pharmaceutical applications. For example, U.S. Pat. No. 5,917,174 to Moore et al. entitled "Device For Assisting The Visually Impaired In Product Recognition And Related Methods" discloses a device that assists visually impaired persons obtain verbal information from consumer product bar codes which contain information about the consumer product such as brand, size, price and ingredients. The device includes a scanner unit to scan a product bar code with electronically stored product information; a processing unit to receive, access, locate, and retrieve corresponding product information from an electronic information storage element such as a computer disk, CD ROM, or hard drive; a voice synthesizer for converting the signal received from the processing unit into audible voice form by a speaker; and a power unit to provide power to the scanner unit and the processing unit.

The device which is the subject of the '174 patent is not without shortcomings for use with medicine containers. The device has the ability to read only one-dimensional product bar codes and, therefore, is not suitable for multi-dimensional bar codes. Thus, it is not practical for medicine containers which require more information than that which is conventionally provided. Additionally, the device is designed to be carried on a belt to assist the user to scan product bar codes during shopping or other related activities. For medicine containers located primarily in the home of the visually impaired user, however, the belt design of the device to be worn by the user is a burden at home and, therefore, not practical for use with medicine containers. In addition, the elements or units of the device are housed in different compartments of the belt. As a result, in operation, the elements or units of the device are interconnected between the different compartments for use with product bar code labels. Moreover, the device does not provide a memory means for storing the bar code information. As a result, if the user desires to re-listen to the information contained in the bar code label, the user must re-scan the bar code label. Thus, the device requires an additional interconnection to operate and is, therefore, potentially vulnerable to become inoperative due to problems with any one of the interconnections.

Other examples of bar code scanning devices for use with educational devices, teller machines, and record/playback devices are disclosed in U.S. Pat. Nos. 5,177,800; 5,616,901 and 5,839,108.

While the prior art teaches the use of bar code scanning devices for many purposes, there is no teaching directed to the special needs of the visually impaired or other or other information challenged persons for use with medicine containers. Accordingly, there is a need and there has never been disclosed a scanning device for use in conjunction with medicine container labels.

OBJECTS AND SUMMARY OF THE INVENTION

It is the primary object of the present invention to provide an apparatus and method of use for scanning devices for use with medicine container labels having individualized information contained on them.

A related object of the present invention is to convert the information contained within the medicine container label into audio and/or visual form for the information challenged person.

Another object of the present invention is to provide a label which has more information provided thereon than prior art labels.

Yet another object of the present invention is to provide a device that enables an information challenged person to scroll between multiple levels of information contained within the medicine container label.

A related object of the invention is to provide an information challenged person with the flexibility to repeatedly re-convey the information contained within the label into audio and/or visual form without having to repeatedly re-scan the entire label.

A further related object of the invention is to provide an information challenged person with essential information regarding the medication.

Another object of the present invention is to provide a scanning device with a memory means to store the information contained in the medicine container label to enable the information challenged person to re-listen to the information without having to re-scan the medicine container label.

Yet another object of the invention is to provide an effective and easy to use means for the information challenged person to determine the contents of the medicine container label that does not interfere with traditional written labels.

Other objects of the present invention will become apparent to persons having ordinary skill in the art to which the present invention pertains from the following description taken in conjunction with the accompanying drawings.

The present invention is an apparatus and method of using a scanning device to permit an information challenged person, such as a visually impaired person, a deaf person, a person with poor eyesight, an illiterate person, etc., to determine the contents of information contained in a label placed on their medicine containers. The apparatus and method comprises a scanning device which includes a processing unit. The scanning device is used to scan or read a label, which is a two-dimensional bar code label or a radio identification (RFID) label, located on the medicine container. The processing unit decodes the information for audio (for visually impaired users, persons with poor eyesight, illiterate persons, etc.) and/or visual dissemination (deaf persons, enlarged font for persons with poor eyesight, illiterate persons in graphics form, etc.) to the person.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 3 is a side perspective view of an alternate embodiment of the scanning device of FIG. 1;

FIG. 4 is a front perspective view of the alternate embodiment of the scanning device shown in FIG. 3;

DETAILED DESCRIPTION OF THE ILLUSTRATED EMBODIMENT

Figure 1:
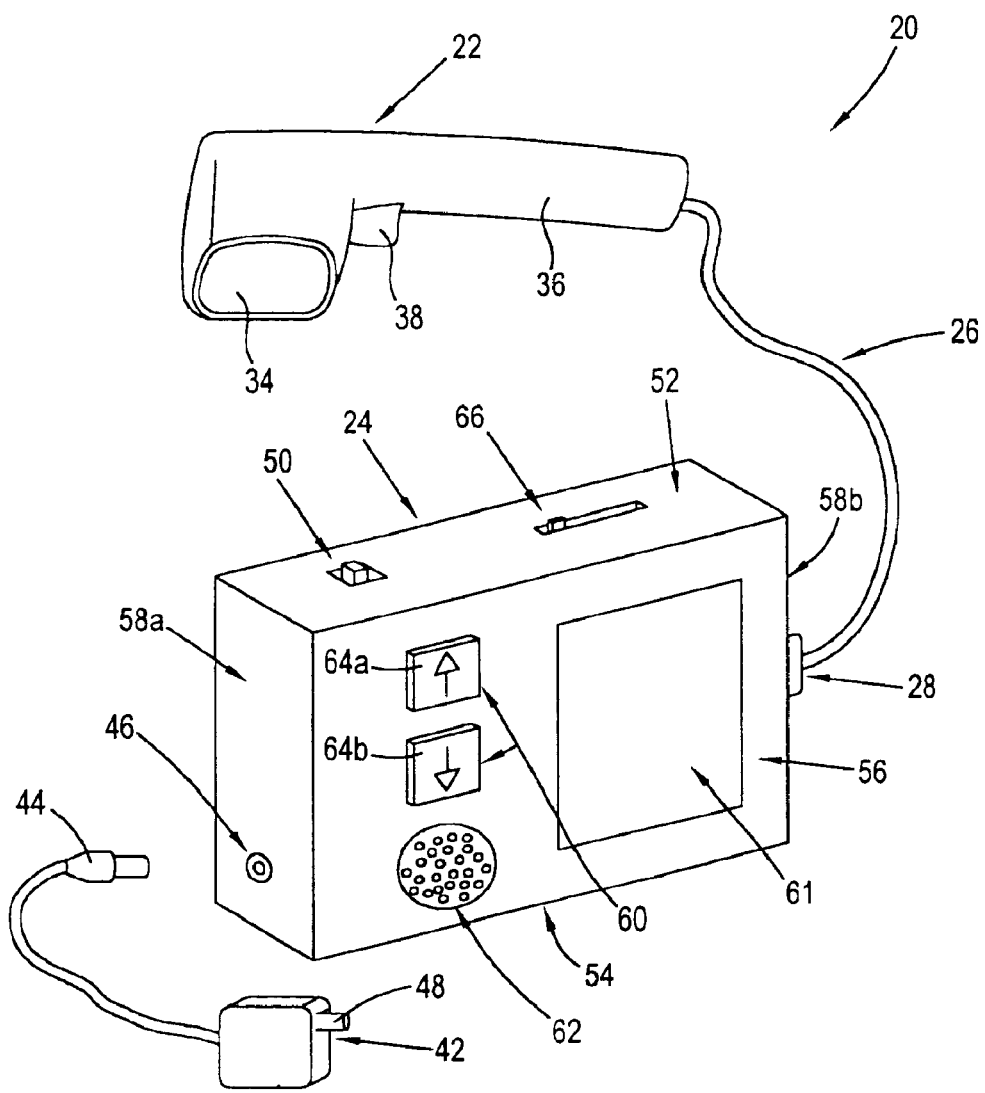
FIG. 1 is a side perspective view of a first embodiment of a scanning device.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Figure 2:
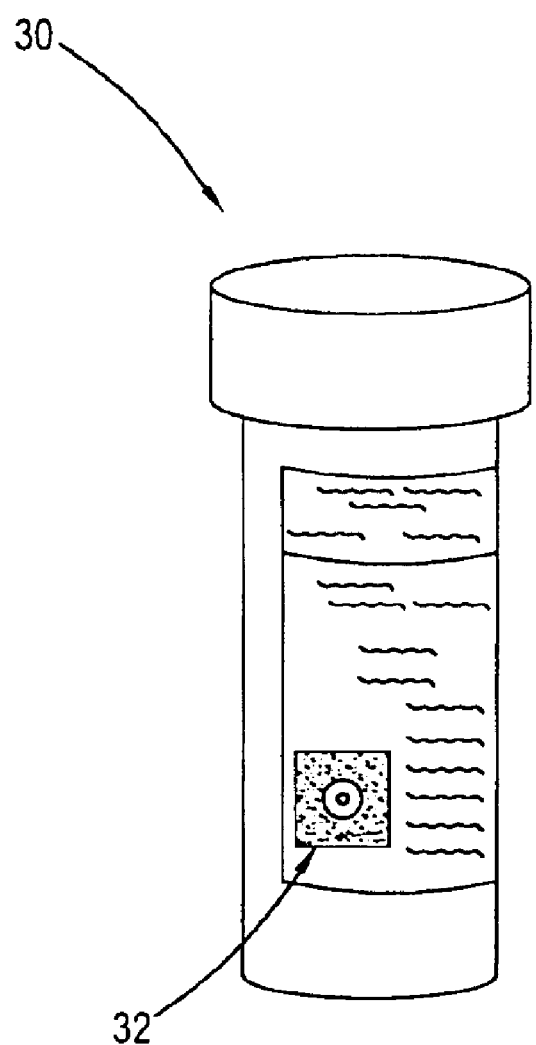
FIG. 2 is front elevational view of a medicine container that contains a two-dimensional bar code label.
Figure 6:
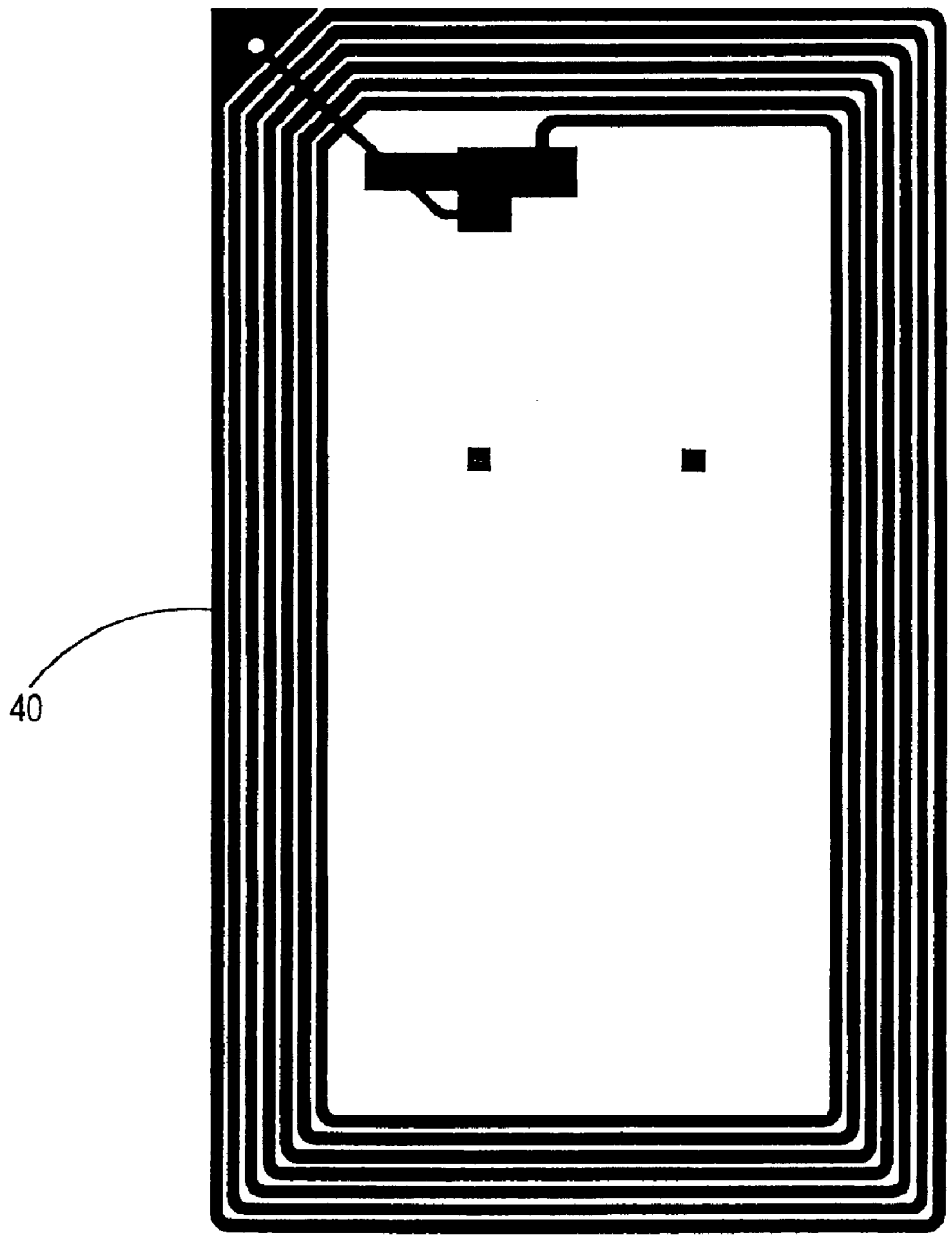
FIG. 6 is a top view of an alternate embodiment of a label which is a radio frequency identification (RFID) label.

The present invention provides a scanning device 20 which is used to scan and decode non-text information provided on a label 32, 40 on a medicine container for an information challenged person. The scanning device 20 includes a reader 22 which scan the label 32, 40 and a processing unit 24 which is used to decode the non-text information provided on the label 32, 40. The label 32 may be a two-dimensional label as shown in FIG. 2 or a radio frequency identification (RFID) label 40 as shown in FIG. 6.

The non-text information on the label 32, 40 contains information regarding the medicine, and preferably contains information that is specifically tailored toward that medication and use by a particular information challenged person. Such information includes, but is not limited to, an identification of the information-challenged person such as the person's name and address, drug reactions regarding the information-challenged person, medical records of the information-challenged person, the present medical condition of the information-challenged person, the past medical condition of the information-challenged person, a physiological trait of the information-challenged person, a characteristic of the information-challenged person; a description of the contents of the container such as the name of the medication and quantity; the prescription number; the name of the prescribing physician; the pharmacy name and phone number; the issue date the discard date; the number of refills; warnings; side effects related to the medicine; a description of conditions of administration of the medicine such as dosage and instructions for use; and instructions regarding accessing information stored in a remotely located database (a database not contained within the scanning device 20).

The term "information challenged person" is defined in the present patent application to mean visually impaired persons, deaf persons, persons with poor eyesight, illiterate persons and other persons which cannot read text.

The term "medication" or "medicine" is defined in the present patent application to mean medicines, drugs or other health restoratives.

While the present invention is described with respect to containers 30, it is to be understood that container 30 is intended to encompass medicine applicators, medicine dispensers, intravenous bags as well.

In a first embodiment of the present invention, see FIGS. 1–5, scanning device 20 is used to scan or read all types of two-dimensional bar code symbologies placed on a medicine container label 32. FIG. 2 shows a medicine container 30 with a two-dimensional bar code label 32 provided thereon. The bar code label 32 may be located anywhere along the exterior of the medicine container 30.

The bar code label 32 contains a two-dimensional symbologies provided on a substrate, such as flexible paper or plastic, which has a self-adhesive side to be affixed to the medicine container 30. Such two-dimensional symbologies include, but are not limited to, Code 49, Code 16K, Data Matrix, Datastrip Code, PDF 417, QR Code, Supercode, and Ultracode. An example of a two-dimensional bar code is one that has the specific information for the medication contained in the symbology provided in multiple adjacent rows that consist of parallel, adjacent bars and spaces, with predetermined width patterns, the arrangement of which represents the particular symbology.

The scanning device 20 includes a reader 22 and a processing unit 24. The reader 22 is connected to the processing unit 24 by a cable 26. Preferably, the cable 26 uses a 9-pin connector 28 to connect to the processing unit 24.

In combination, the reader 22 and the processing unit 24 coact to determine the non-text contents of the label 32 and to supply the specific information contained within label 32 to the information challenged person. The reader 22 acts as an input device that uses electro-optical techniques to scan the non-text contents of the label 32. The processing unit 24 acts as a decoder, processor and storer of the information contained within the label 32. The processing unit 24 receives and analyses the signal produced by the reader 22, decodes the information encoded in the label 32, and provides the decoded information for audio and/or visual dissemination to the information challenged person. The processing unit 24 also stores the decoded information from the label 32 in a memory provided as part of the processing unit 24.

The reader 22 has a reader face 34, a handle 36, and an activation button 38. The reader 22, through the reader face 34, optically transmits light energy to the label 32 and receives reflected light from the label 32. The process by which the reader 22 transmits and receives light energy from the label 32 is commonly referred to as "scanning". Typically, scanning is accomplished by aligning the reader face 34 with the label 32 and transmitting light energy in a smooth transition across the label 32 from the outermost left portion of the label 32 to the outermost right portion of the label 32 such that the entire label 32 is scanned by the reader 22.

Preferably, the reader face 34 is flat. The handle 36 provides the information challenged person with a means to hold the reader 22 and to direct the reader face 34 toward the label 32 and to scan the label 32. Preferably, the handle 36 of the reader 22 is circular in shape to conform to the natural grip of the information challenged person.

Alternatively, the reader 22 can be in other shapes and sizes provided that the reader 22 is ergonomic to the information challenged person and provides an effective means to scan the label 32. The activation button 38 activates and deactivates the transmission of the optical light energy from the reader 22. Preferably, the reader face 34, the handle 36 and the activation button 38 are located on the same side of the reader 22 to provide the easiest and most efficient means to scan the label 32.

As shown in FIG. 1, the processing unit 24 preferably is rectangular in shape with a top 52, a bottom 54, a front 56, and sides 58a, 58b. The processing unit 24 is powered by a power unit 42. In the preferred embodiment, the power unit 42 is a digital current power converter. The power unit 42 has a plug 44 at one end and terminals 48 located at the other end. The plug 44 of the power unit 42 is received into a port 46 located on the side 58a within the processing unit 24. Preferably, the port 46 is located on the opposite side of the processing unit 24 as a 9-pin connector 28 and a cable 26 are located on side 58b. The terminals 48 are inserted into an electrical outlet source (not illustrated) to provide, through the power unit 42, electrical power to the scanning device 20.

Figure 5:
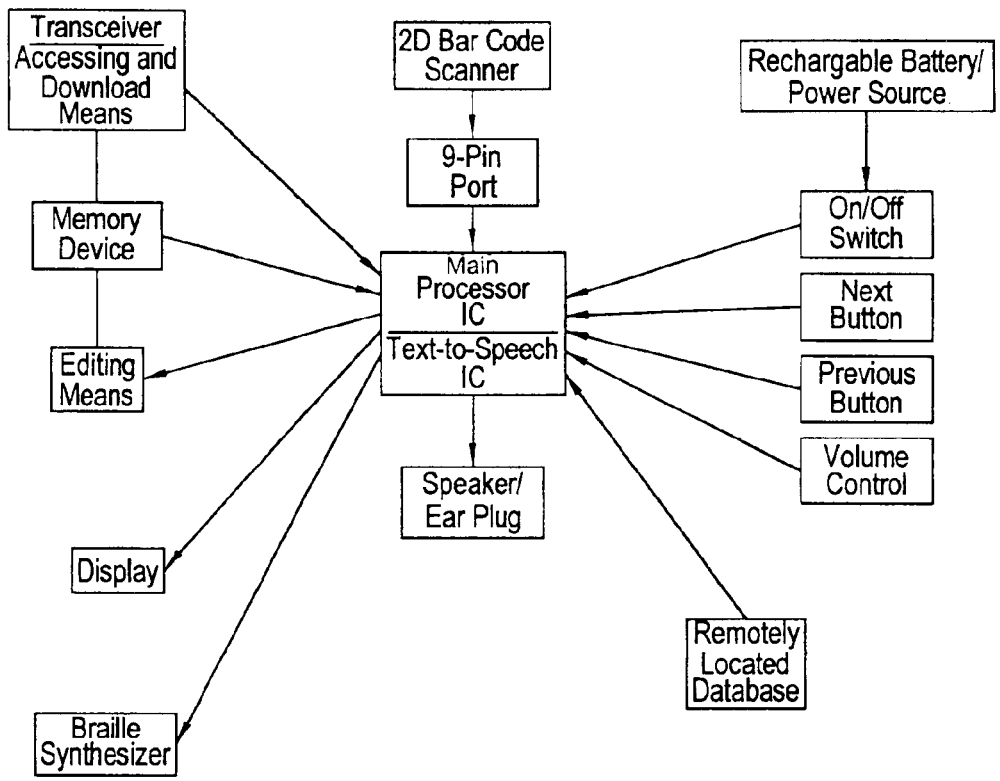
FIG. 5 is a block diagram of the interrelationship of the parts of the scanning device of FIGS. 1–4 and peripheral devices.

As shown in FIG. 5, the processing unit 24 includes a transceiver and a memory coupled thereto. The transceiver can receive data from a remotely located database and can transmit data stored in the memory to the remotely located database.

The processing unit 24 includes means for accessing and downloading data, which functions with the transceiver, from the remotely located database into the memory of the processing unit 24. The means for accessing and downloading data is implemented using suitable circuity and, software. The processing unit 24 also includes means for editing the information in the memory of the processing unit 24. The editing means is implemented using suitable circuity and software. Information stored in the memory of the processing unit 24 can be used to accomplish the editing of the information in the memory. The information in the memory of the processing unit 24 can be edited upon examination of a change in the health in the information challenged person.

The remotely located database is not contained within the scanning device 20. The remotely located database can be a global computer network commonly referred to as the Internet®, can be a remote database maintained on site by a care giver, the information challenged person, or the like.

To control the electrical power to the processing unit 24 and the reader 22 from the power unit 42, an on/off switch 50 is provided on the top 52 of the processing unit 24. The switch 50 is located on the top 52 of the processing unit 24 to provide easy access by the information challenged person. Situated on the front 56 of the processing unit 24 are buttons 60, a speaker 62 and a video display 61. The buttons 60 provide the information challenged person with the ability to scroll between the multiple levels of information contained within the label 32. Depressing button 60 with arrow 64a causes the next succeeding level of information to be displayed in audio form through speaker 62 (text-to-speech processing is discussed in detail below) and/or in video form through the display 61 to the information challenged person. Audio form is preferred for visually impaired persons, persons with poor eyesight, illiterate persons. Video form is preferred for deaf persons. Video can be provided to a person with poor eyesight in an enlarged font for easier reading or to an illiterate person when the display is in graphics form. Conversely, depressing button 60 with arrow 64b causes the preceding level of information to be displayed in audio form through speaker 62 and/or video form through the display 61 to the information challenged person. The volume tone of the audio from speaker 62 is controlled by volume control lever 66. Alternatively, the information can be played back randomly, if desired.

A Braille synthesizer can be connected to the processing unit 24 for outputting the information in Braille.

As shown in FIGS. 3 and 4, the scanning device 20 may be designed into a single housing of the shape of the reader 22. In this embodiment, the processing unit 24 is incorporated into the reader 22 to form the scanning device 20. The elements of the reader 22 and the processing unit 24 remain unchanged, but given the different shape of the scanning device 20, the elements are provided in different positions for efficient and ergonomic use by the information challenged person. The locations of the reader face 34, the handle 36, and the activation button 38 remain unchanged. The handle 36 of the reader 22 is provided with the port 46 at one end to receive the plug 44 of the power unit 42. Adjacent to the port 46 is a battery compartment 68. Preferably, the battery compartment 68 holds a battery to power the scanning device 20 when the scanning device 20 is not attached to the power unit 42. Alternatively, the battery compartment 68 may hold multiple batteries. Located on the same-side of the battery compartment 68 of the handle 36 and opposite the reader face 34 are buttons 60, the speaker 62 and the display 61. Adjacent to display 61 is a volume control dial 66. The buttons 60, the speaker 62, the display 61 and the volume control dial 66 are positioned such that its use and function is not impeded due to the grip of the information challenged person on the handle 36 when the scanning device 20 is in use.

In a second embodiment of the present invention, see FIGS. 6–9, a scanning device 20 is used to scan or read a radio frequency identification (RFID) label 40 placed on a medicine container (such as the medicine container 30 show in FIG. 2). RFID labels 40 are commonly referred to as "smart labels". The RFID label 40 contains the same information as the two-dimensional bar code label 32.

Typically, an RFID label 40 is paper-thin with a programmable integrated circuit, a transceiver, and an antenna mounted on a substrate, such as flexible paper or plastic, which has a self-adhesive side to be affixed to the medicine container. The RFID label 40 may be located anywhere along the exterior of the medicine container 30. The RFID label 40 communicates through radio frequency signals with the scanning device 20.

The RFID label 40 require a memory capacity of between 1.5 kilobytes and 2.0 kilobytes to provide typical prescription information. Alternatively, to reduce memory capacity or maintain a memory capacity of 1.5 kilobytes to 2.0 kilobytes, some prescription information may be coded as data onto a microchip within the processing unit 24 for use as a corresponding data table to determine and decode the information. Preferably, the pharmacist has a radio frequency identification software and corresponding printer to create the radio frequency identification labels 40 to fulfill a prescription at the pharmacy.

Figure 7:
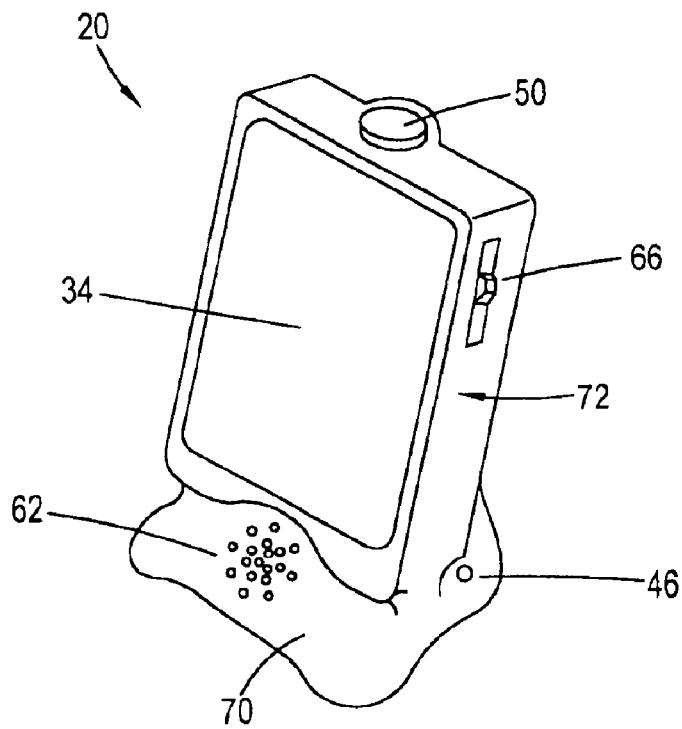
FIG. 7 is a side perspective view of an alternate embodiment of a scanning device for use with a radio frequency identification labels.
Figure 8:
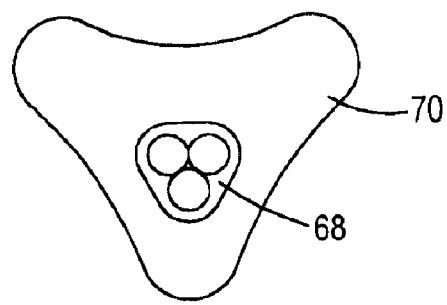
FIG. 8 is a bottom view of the alternate embodiment of the scanning device shown in FIG. 7.

The scanning device 20 may be designed in any shape or size, preferably, as illustrated in FIGS. 7 and 8. Alternatively, the scanning device 20 may be any other shape or size so long as the scanning device 20 may effectively read the RFID label 40.

Figure 9:
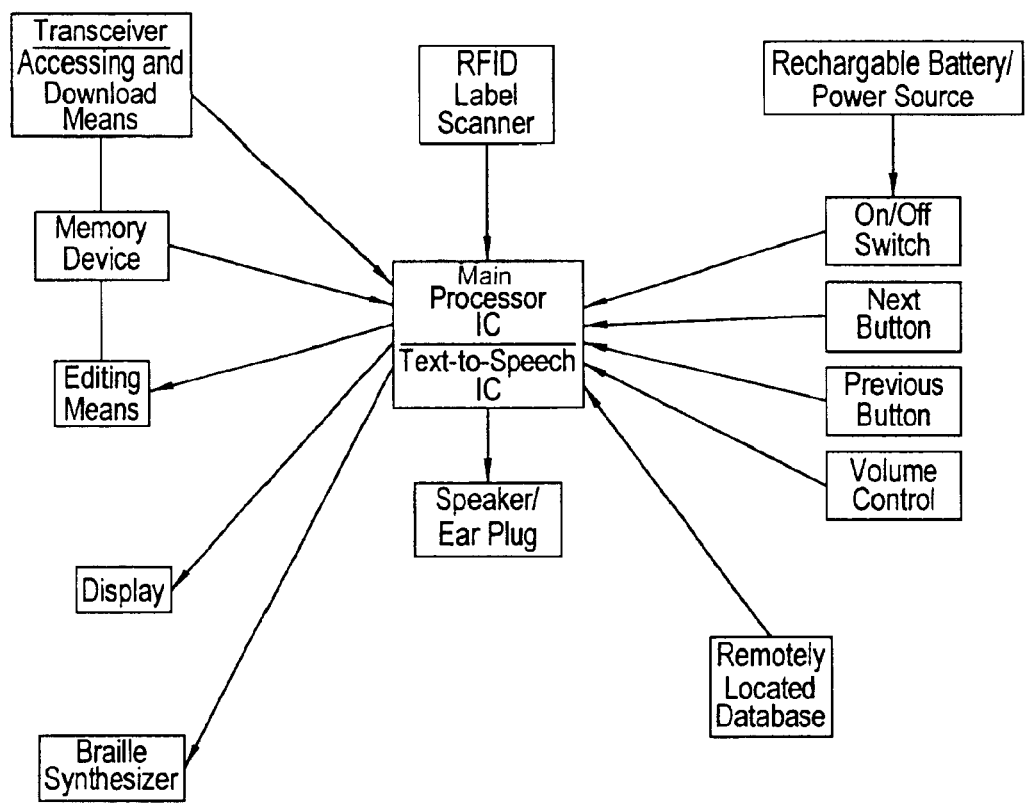
FIG. 9 is a block diagram of the interrelationship of the parts of the alternate embodiment of the scanning device shown in FIGS. 7 and 8 and peripheral devices.

The scanning device 20 which is used with the RFID label 40 includes all the same elements of the first embodiment, see FIG. 9, and is further provided with the additional advantage of a base 70 and a backing 72, see FIGS. 7 and 8. The base 70 serves to support the scanning device 20 and permit the scanning device 20 to be placed on any flat surface within the home of the information challenged person. In this position, the backing 72 extends from the base 70 such that the reader face 34 has its greatest exposure to emit radio frequencies and, thereby, provide maximum readability of the RFID label 40 on the medicine container.

The editing means in this alternate embodiment also includes means for editing the information in the memory of the RFID label 40. The editing means is implemented using suitable circuity and software. Information stored in the memory of the processing unit 24 can be used to accomplish the editing of the information in the memory of the label 40. The transceiver in the scanning device 20 further communicates with the transceiver in the RFID label 40.

In use, the RFID label 40 provides certain advantages over labels having two-dimensional bar codes thereon. First, the scanning device 20 uses radio waves instead of optical light energy to read the RFID label 40 and, therefore, permit the RFID label 40 to be read over a larger distance than the two-dimensional bar code labels 32. Second, the radio frequency identification is not based on alignment or line-of-sight technology and, therefore, the RFID label 40 is able to be read through snow, fog, paint, grime, traditional print labels and other environmentally challenging conditions. This is particularly useful for the visually impaired as the desired medicine container may be located and read anywhere in the home of the information challenged person. Third, the RFID label 40 is capable of being modified or reprogrammed without the need to create another label. Fourth, the RFID label 40 collects energy from the radio frequency field and, therefore, is capable of operating without batteries or a power unit.

In each embodiment, the scanning device 20 can be part of a mobile telephone or wireless organizer. This is especially helpful when the scanning device 20 is used to access information in the remote database. The mobile telephone includes data processing means and conversion software which controls the data processing means. The software is configured so as to allow an information challenged person to employ the telephone functions when in telephone mode to control data retrieval functions.

Figure 10:
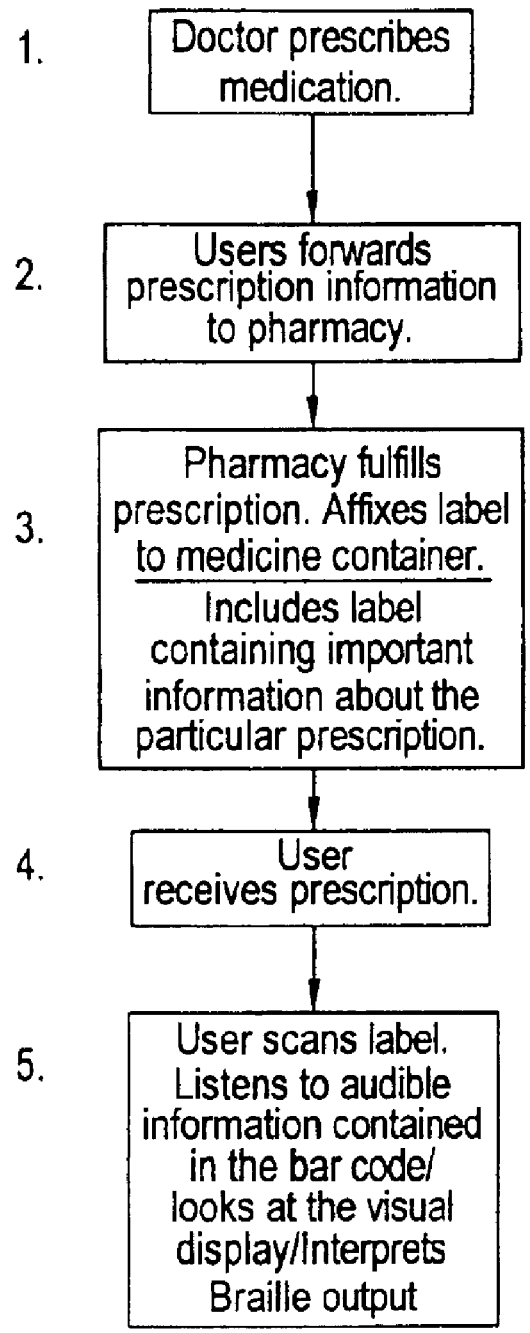
FIG. 10 is a flow chart of the method for creating the a label for the medicine container and for use with the scanning device by an information challenged person.

FIG. 10 depicts the method by which the label 32, 40 is created and the contents of the label 32, 40 are determined by the information challenged person with the scanning device 20. In step 1, the doctor prescribes a medication to the information challenged person. In step 2, the doctor orders the medication from a pharmacy and provides the pharmacist with the information to fulfill the prescribed order. In step 3, the pharmacist fulfills the prescription and places the prescribed medication in a medicine container 30. The pharmacist then creates the label 32 containing the two-dimensional bar code or the RFID label 40, with information particular to the information challenged person and medication provided by the doctor. The pharmacist then affixes the label 32, 40 to the exterior of the medicine container 30. In step 4, the information challenged person receives the prescribed and filled medication from the pharmacist. In step 5, the information challenged person uses the scanning device 20 to scan the label 32 on the medicine container 30.

Figure 11:
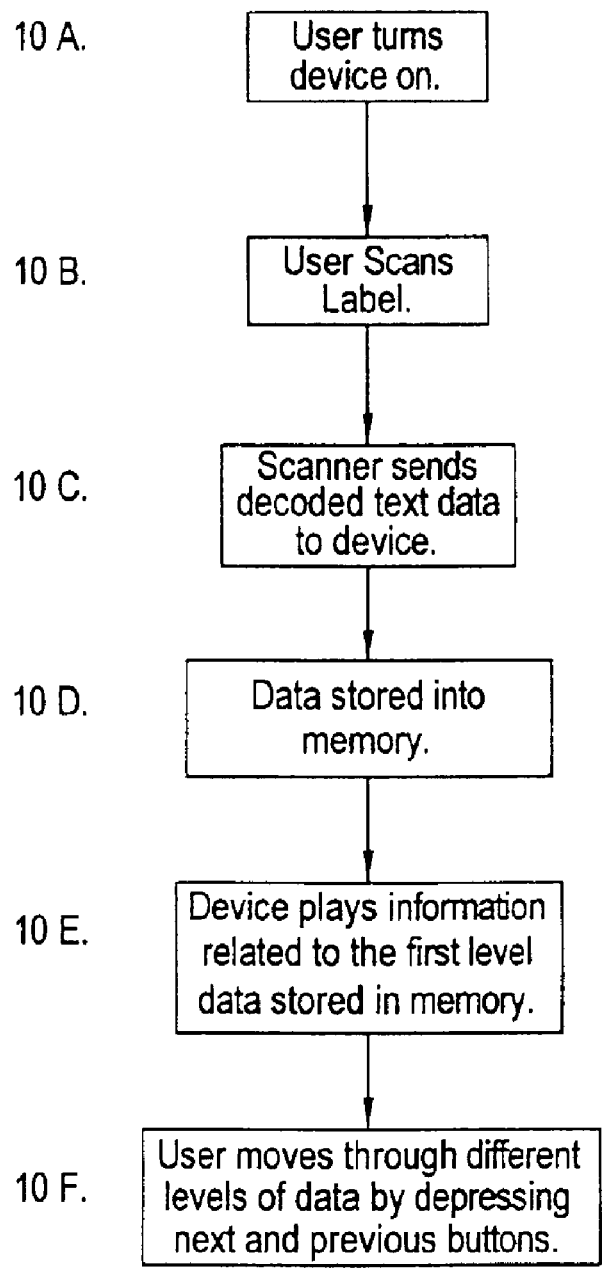
FIG. 11 is a flow chart of the method for using the scanning device with the label contained on the medicine container.

Step 5 is divided into six subparts, as illustrated in FIG. 11, when the information challenged person desires to determine the information on the medicine container label 32, 40 with the scanning device 20.

In subpart 10A, the information challenged person obtains the scanning device 20 and toggles the switch 50 into the "on" position to permit power to the scanning device 20 either through the power unit 42 or the batteries.

In subpart 10B, the information challenged person scans the label 32, 40. If a two-dimensional bar code label 32 is used, the information challenged person grips the handle 36 of the reader 22 and directs the reader face 34 directly toward the label 32 the on medicine container 30. Upon alignment of the reader face 34 to the label 32, the information challenged person depresses the activation button 38. Upon depression of the activation button 38, the reader 22 optically transmits light energy to the label 32. The light energy is reflected from the bar code label 32. The amount of reflected light received by the reader 22 varies according to symbology on the bar code. With regard to subpart 10B, if a RFID label 40 is used, the information challenged person brings the scanning device 20 and the medicine container into proximity and the scanning device scans the label.

In subpart 10C, the reader 22 transfers the received encoded information to the processing unit 24.

In subpart 10D, the processing unit 24 decodes the encoded information into text format and stores the decoded text information into the memory of the processing unit 24. Preferably, the processing unit 24 uses a processor to decode the encoded information. For the type of two-dimension bar code which is comprises of bars and spaces, the processor must determine whether the signal received is on a bar or a space, measure the width of the bars and spaces of the symbol, quantize the element widths of the symbol, decode the encoded data in the symbol by comparing the quantized element widths to a table of values corresponding to a character set provided within the processor, and if necessary, reverse the order of the decoded data characters to accommodate symbols that have been scanned right to left.

In subpart 10E, the processing unit 24 reads, from the memory, the first level of decoded text information in audio form through speaker 62 or in video form through the display 61 to the information challenged person.

In subpart 10F, the information challenged person may depress arrow 64a of button 60 to scroll through and listen to the next succeeding levels of information. For example, if the first level of information was just listened to, the information challenged person may depress arrow 64a of button 60 to listen to the second level of information, then the third level of information, and so on. The information challenged person may also depress arrow 64b of button 60 to scroll in reverse order and listen to the preceding levels of information. For example, if the third level of information was just listened to, the information challenged person may depress arrow 64b of button 60 to listen to the second level of information' again, and then the first level of information, if desired.

In one type of two-dimensional bar codes, multiple adjacent rows of parallel, adjacent bars and spaces, with predetermined width patterns are arranged in a particular symbology. Each row represents a different level of information specific to the medication and is encoded in the symbol of bar code label 32. For example, row 1 may represent a first level of information such as patient name, prescription number, drug name, size, quantity, dosage, and instructions for use; row 2 may represent a second level of information such as doctor name, pharmacy name and phone number, issue date, and discard date; row 3 may represent a third level of information such as number of refills, warnings, and side effects; and so on.

Importantly, the information provided on the label 32, 40 can contain instructions regarding accessing information stored in a remotely located database. This can be provided as a link to an applicable web site.

If the information challenged person wishes to repeat information obtained from a label 32, 40, the label 32, 40 does not need to be re-scanned. The scanning device 20 stores the information in the memory for repeat audio output and/or video output.

The decoded text information that resides in the memory of the processing unit 24 and which is listened to by the information challenged person can be converted to audio speech, for dissemination through speaker 62, by an embedded text-to-speech processor. Examples of text-to-speech processors include TMS320C203 from Texas Instruments, V8600 from RC Systems, and MSM7630 from OKI Semiconductor.

While the two-dimensional bar code, and the transceiver and memory have been described as being provided on a substrate which is mounted on the container 30, it is to be understood that the symbology and the transceiver and memory can directly integrated into the structure of the container 30.

While the invention has been described in conjunction with a specific embodiment, it is evident that many alternatives, modifications and variations will be apparent to those skilled in the art in light of the foregoing description. Accordingly, it in intended to embrace all such alternatives, modifications and variations as fall within the spirit and scope of the appended claims.

The invention claimed is:

1. A combination comprising:
   a label, a two dimension bar code provided on said label, said two dimension bar code containing information related to medicine being taken by an information-challenged person; and
   a retrieval device, said retrieval device including means for retrieving data from said two dimension bar code, means for interpreting said retrieved data, and means for conveying said interpreted data to the information-challenged person in a form understandable to the information-challenged person, said means for conveying comprising a speech synthesizer which is capable of converting said interpreted data into audible speech.

2. The combination as defined in claim 1, wherein said two dimension bar code has data thereon including at least one of a description of the medicine, an identification of the information-challenged person, an identification of a physician prescribing said medicine; drug reactions regarding the information-challenged person, medical records of the information-challenged person, side effects related to said medicine, the present medical condition of the information-challenged person, the past medical condition of the information-challenged person, a physiological trait of the information-challenged person, a characteristic of the information-challenged person, a description of conditions of administration of the medicine; and instructions regarding accessing information stored in a remotely located database.

3. The combination as defined in claim 1, wherein said retrieval device further includes means for storing said data retrieved from said label.

4. The combination as defined in claim 1, wherein said conveying means is capable of scrolling through said interpreted data when conveyed to the information-challenged person.

5. The combination as defined in claim 1, wherein said conveying means is capable of randomly playing said interpreted data when conveyed to the information-challenged person.

6. The combination as defined in claim 1, wherein said retrieval device further includes a transmitter for transmitting said retrieved data to a remotely-located database.

7. A combination comprising:
   a label, a two dimension bar code provided on said label, said two dimension bar code containing information related to medicine being taken by an information-challenged person; and
   a retrieval device, said retrieval device including means for retrieving data from said two dimension bar code, means for interpreting said retrieved data, and means for conveying said interpreted data to the information-challenged person in a form understandable to the information-challenged person, said retrieval device is a mobile telephone.

8. A combination comprising:
   a label, a two dimension bar code provided on said label, said two dimension bar code containing information related to medicine being taken by an information-challenged person; and
   a retrieval device, said retrieval device including means for retrieving data from said two dimension bar code, means for interpreting said retrieved data, and means for conveying said interpreted data to the information-challenged person in a form understandable to the information-challenged person, said retrieval device is a wireless organizer.

9. The combination as defined in claim 7, wherein said mobile telephone includes a memory, and means for accessing information from a remote database and storing said information in said memory.

10. The combination as defined in claim 1, wherein said conveying means comprises a display for visually displaying said interpreted data in alphabetical characters.

11. A combination comprising:
   a label, a two dimension bar code provided on said label, said two dimension bar code containing information related to medicine being taken by an information-challenged person; and a retrieval device, said retrieval device including means for retrieving data from said two dimension bar code, means for interpreting said retrieved data, and means for conveying said interpreted data to the information-challenged person in a form understandable to the information-challenged person, said conveying means comprising a display for visually displaying said interpreted data in graphics.

12. A combination comprising:

a label, a two dimension bar code provided on said label, said two dimension bar code containing information related to medicine being taken by an information-challenged person; and a retrieval device, said retrieval device including means for retrieving data from said two dimension bar code, means for interpreting said retrieved data, and means for conveying said interpreted data to the information-challenged person in a form understandable to the information-challenged person, said conveying means comprising a Braille synthesizer.

13. A combination comprising:

a radio frequency identification label code containing information related to medicine being taken by an information-challenged person; and a retrieval device, said retrieval device including means for retrieving data from said radio frequency identification label, means for interpreting said retrieved data, and means for conveying said interpreted data to the information-challenged person in a form understandable to the information-challenged person.

14. The combination as defined in claim 13, wherein said radio frequency identification label includes a memory and a transceiver coupled to said memory, said transceiver being capable of receiving data and storing said data in said memory, and further being capable of retrieving said data stored in said memory and transmitting said data.

15. The combination as defined in claim 13, wherein said information includes at least one of a description of the medicine, an identification of the information-challenged person, an identification of a physician prescribing said medicine; drug reactions regarding the information-challenged person, medical records of the information-challenged person, side effects related to said medicine, the present medical condition of the information-challenged person, the past medical condition of the information-challenged person, a physiological trait of the information-challenged person, a characteristic of the information-challenged person, a description of conditions of administration of the medicine; and instructions regarding accessing information stored in a remotely located database.

16. The combination as defined in claim 13, wherein said retrieval device includes means for editing said data in said memory.

17. The combination as defined in claim 13, wherein said retrieval device further includes means for storing said data retrieved from said label.

18. The combination as defined in claim 13, wherein said conveying means is capable of scrolling through said data when conveyed to the information-challenged person.

19. The combination as defined in claim 13, wherein said conveying means is capable of randomly playing said data when conveyed to the information-challenged person.

20. The combination as defined in claim 13, wherein said retrieval device further includes a transmitter for transmitting said data to a remotely-located database.

21. The combination as defined in claim 13, wherein said retrieval device is a mobile telephone.

22. The combination as defined in claim 13, wherein said retrieval device is a wireless organizer.

23. The combination as defined in claim 13, wherein said retrieval device includes a retrieval device memory, and means for accessing information from a remote database and storing said information in said retrieval device memory.

24. The combination as defined in claim 23, wherein said retrieval device is a mobile telephone.

25. The combination as defined in claim 23, wherein said retrieval device is a wireless organizer.

26. The combination as defined in claim 13, wherein said conveying means comprises a speech synthesizing means for converting said data into audible speech.

27. The combination as defined in claim 13, wherein said conveying means comprises a display for visually displaying said interpreted data in alphabetical characters.

28. The combination as defined in claim 13, wherein said conveying means comprises a display for visually displaying said interpreted data in graphics.

29. The combination as defined in claim 13, wherein said conveying means comprises a Braille synthesizer.

30. A combination comprising:

a container, non-text data provided on said container, said non-text data containing information related to medicine being taken by an information-challenged person; and a retrieval device, said retrieval device including means for retrieving said non-text data from said container, means for interpreting said non-text data, and means for conveying said non-text data to the information-challenged person in a form understandable to the information-challenged person, said conveying means comprising a speech synthesizer for converting said data into audible speech.

31. The combination as defined in claim 30, wherein said non-text data is provided in a memory provided on said container, said container further including a transceiver coupled to said memory, said transceiver being capable of receiving data and storing said non-text data in said memory, and further being capable of retrieving said non-text data stored in said memory and transmitting said non-text data.

32. The combination as defined in claim 31, wherein the non-text data includes at least one of a description of the medicine, an identification of the information-challenged person, an identification of a physician prescribing said medicine; drug reactions regarding the information-challenged person, medical records of the information-challenged person, side effects related to said medicine, the present medical condition of the information-challenged person, the past medical condition of the information-challenged person, a physiological trait of the information-challenged person, a characteristic of the information-challenged person, a description of conditions of administration of the medicine; and instructions regarding accessing information stored in a remotely located database.

33. The combination as defined in claim 31, wherein said memory and said transceiver are provided on a label which is mounted on said container.

34. The combination as defined in claim 31, wherein said retrieval device includes means for editing said data in said memory.

35. The combination as defined in claim 30, wherein the non-text data includes at least one of a description of the medicine, an identification of the information-challenged person, an identification of a physician prescribing said medicine; drug reactions regarding the information-challenged person, medical records of the information-challenged person, side effects related to said medicine, the present medical condition of the information-challenged person, the past medical condition of the information-challenged person, a physiological trait of the information-challenged person, a characteristic of the information-challenged person, a description of conditions of administration of the medicine; and instructions regarding accessing information stored in a remotely located database.

36. The combination as defined in claim 30, wherein said retrieval device further includes means for storing said non-text data retrieved from container.

37. The combination as defined in claim 30, wherein said conveying means is capable of scrolling through said data when conveyed to the information-challenged person.

38. The combination as defined in claim 30, wherein said conveying means is capable of randomly playing said data when conveyed to the information-challenged person.

39. The combination as defined in claim 30, wherein said retrieval device further includes a transmitter for transmitting said data to a remotely-located database.

40. A combination comprising:
   a container, non-text data provided on said container, said non-text data containing information related to medicine being taken by an information-challenged person; and
   a retrieval device, said retrieval device including means for retrieving said non-text data from said container, means for interpreting said non-text data, and means for conveying said non-text data to the information-challenged person in a form understandable to the information-challenged person, said retrieval device is a mobile telephone.

41. A combination comprising:
   a container, non-text data provided on said container, said non-text data containing information related to medicine being taken by an information-challenged person; and
   a retrieval device, said retrieval device including means for retrieving said non-text data from said container, means for interpreting said non-text data, and means for conveying said non-text data to the information-challenged person in a form understandable to the information-challenged person, said retrieval device is a wireless organizer.

42. The combination as defined in claim 40, wherein said mobile telephone includes a memory, and means for accessing information from a remote database and storing said information in said memory.

43. The combination as defined in claim 30, wherein said conveying means comprises a display for visually displaying said interpreted data in alphabetical characters.

44. A combination comprising:
   a container, non-text data provided on said container, said non-text data containing information related to medicine being taken by an information-challenged person; and
   a retrieval device, said retrieval device including means for retrieving said non-text data from said container, means for interpreting said non-text data, and means for conveying said non-text data to the information-challenged person in a form understandable to the information-challenged person, said conveying means comprising a display for visually displaying said interpreted data in graphics.

45. A combination comprising:
   a container, non-text data provided on said container, said non-text data containing information related to medicine being taken by an information-challenged person; and
   a retrieval device, said retrieval device including means for retrieving said non-text data from said container, means for interpreting said non-text data, and means for conveying said non-text data to the information-challenged person in a form understandable to the information-challenged person, said conveying means comprising a Braille synthesizer.

46. The combination as defined in claim 8, wherein said wireless organizer includes a memory, and means for accessing information from a remote database and storing said information in said memory.

47. The combination as defined in claim 41, wherein said wireless organizer includes a memory, and means for accessing information from a remote database and storing said information in said memory.

* * * * *

UNITED STATES PATENT AND TRADEMARK OFFICE
CERTIFICATE OF CORRECTION

PATENT NO. : 6,877,658 B2
DATED : April 12, 2005
INVENTOR(S) : David Raistrick and Phillip Raistrick It is certified that error appears in the above-identified patent and that said Letters Patent is hereby corrected as shown below:

Column 11,
Line 22, "label code containing" should be -- label containing --.

Signed and Sealed this

Twenty-seventh Day of September, 2005

JON W. DUDAS
*Director of the United States Patent and Trademark Office*